(12) United States Patent
Ezaki et al.

(10) Patent No.: US 7,943,299 B2
(45) Date of Patent: May 17, 2011

(54) METHOD FOR DETERMINING NUCLEOTIDE SEQUENCES

(75) Inventors: Satoshi Ezaki, Ibaragi (JP); Stefanie Häfele, Freiburg (DE); Till Bachmann, Stuttgart (DE); Rolf D. Schmid, Stuttgart (DE)

(73) Assignee: Eppendorf AG, Hamburg (DE)

( * ) Notice: Subject to any disclaimer, the term of this patent is extended or adjusted under 35 U.S.C. 154(b) by 631 days.

(21) Appl. No.: 10/408,494

(22) Filed: Apr. 7, 2003

(65) Prior Publication Data

US 2004/0053286 A1 Mar. 18, 2004

(30) Foreign Application Priority Data

Apr. 8, 2002 (DE) .................................. 102 15 367

(51) Int. Cl.
*C12Q 1/68* (2006.01)
*C12M 1/34* (2006.01)
*C07K 14/435* (2006.01)

(52) U.S. Cl. .......................... 435/6; 435/287.2; 530/350

(58) Field of Classification Search .................... None
See application file for complete search history.

(56) References Cited

U.S. PATENT DOCUMENTS 6,642,000 B1 * 11/2003 Strizhkov et al. ................. 435/6

FOREIGN PATENT DOCUMENTS

EP 1055735 A2 * 11/2000

OTHER PUBLICATIONS

Bakalkin, G. et al. p53 binds single-stranded DNA ends and catalyzes DNA renaturation and strand transfer. Proc. Natl. Acad. Sci. USA 91:413-417 (Jan. 1994).*
Westin, L. et al. Antimicrobial resistance and bacterial identification utilizing a microelectronic chip array. Journal of Clinical Microbiology 39(3):1097-1104 (Mar. 2001).*
Anderson, M. and Young, B. "Quantitative filter hybridization," pp. 73-111 in "Nucleic acid hybridization a practical approach," Hames and Higgins, eds., 1991.*
Piao, X. et al. Effects of mismatches and insertions on discrimination accuracy of nucleic acid probes. Acta Biochimica Polonica 55:713-720 (2008).*

* cited by examiner

*Primary Examiner* — Diana B Johannsen
(74) *Attorney, Agent, or Firm* — K&L Gates LLP

(57) ABSTRACT

The present invention relates to an improved method for determining nucleotide sequences or nucleotide sequences on biochips/micro-assays, for example, using p53 mediated hybridization. The present invention relates particularly to the use of p53 polypeptides in determining changes in nucleotide sequences.

11 Claims, 7 Drawing Sheets

A
B
Fig. 2
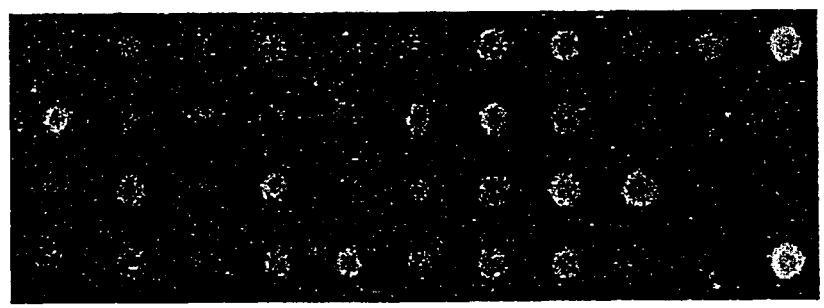
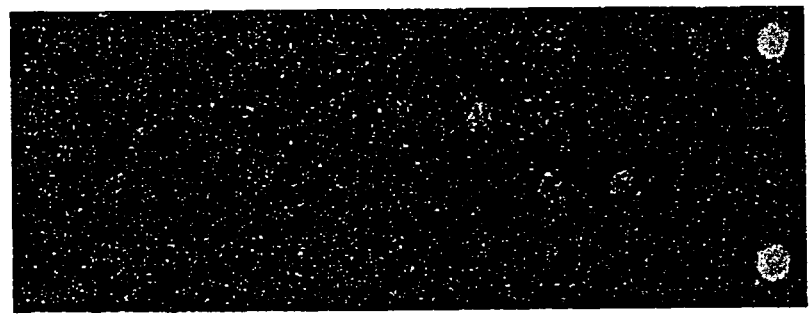

Printing of the PCR Product Micro-Array
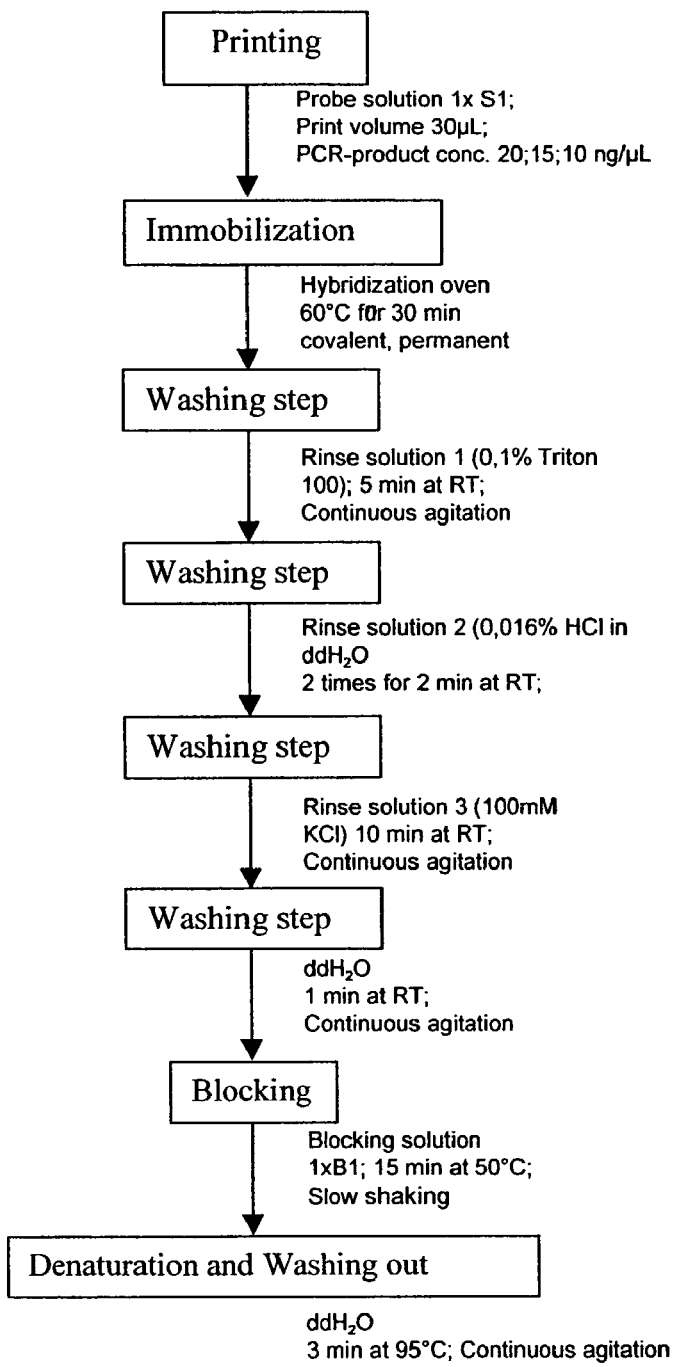
Fig. 4 Printing Scheme for Micro-Arrays with aminomodified PCR-Products

|  | Sense aminomod. | Anti-sense aminomod. | Bilaterally Aminomod. | Cy5 sense aminomod. | | | | |
|---|---|---|---|---|---|---|---|---|
| 20µM Ampicillin | ● | ● | ● | ● | ● | ● | ● | ● |
| 20µM Tetrazyklin | ○ | ○ | ○ | ○ | ○ | ○ | ○ | ○ |
| 20µM pORF-p53 | ○ | ○ | ○ | ○ | ○ | ○ | ○ | ○ |
| 20µM AChE | ○ | ○ | ○ | ○ | ○ | ○ | ○ | ○ |
| 15µM Ampicillin | ● | ● | ● | ● | ● | ● | ● | ● |
| 15µM Tetrazyklin | ○ | ○ | ○ | ○ | ○ | ○ | ○ | ○ |
| 15µM pORF-p53 | ○ | ○ | ○ | ○ | ○ | ○ | ○ | ○ |
| 15µM AChE | ○ | ○ | ○ | ○ | ○ | ○ | ○ | ○ |
| 10µM Ampicillin | ● | ● | ● | ● | ● | ● | ● | ● |
| 10µM Tetrazyklin | ○ | ○ | ○ | ○ | ○ | ○ | ○ | ○ |
| 10µM pORF-p53 | ○ | ○ | ○ | ○ | ○ | ○ | ○ | ○ |
| 10µM AChE | ○ | ○ | ○ | ○ | ○ | ○ | ○ | ○ |

Fig. 5: Layout of all Variants of Unilateral Amino-modified / Bilateral Amino-modified PCR Products in 3 x SSC and 1.5 M Betain.

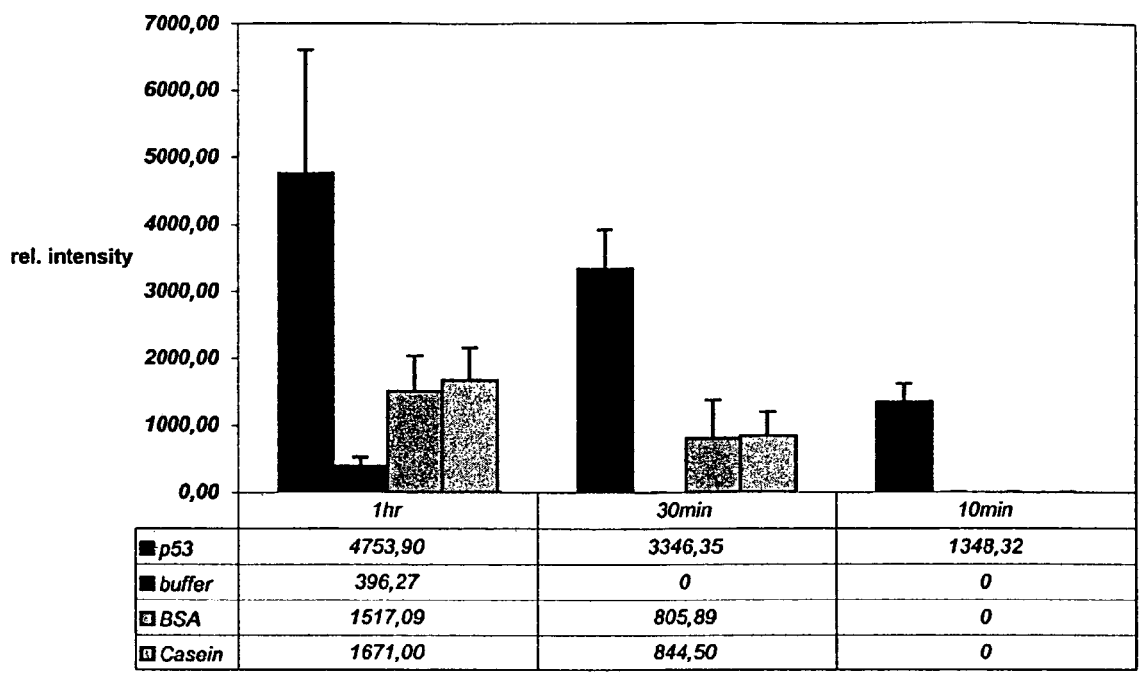
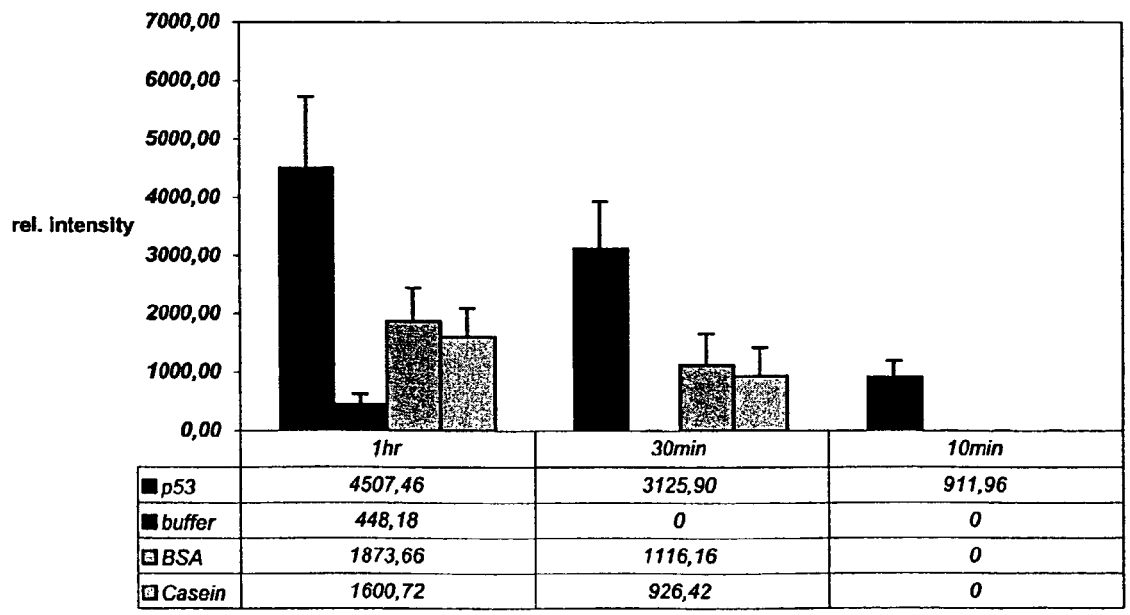
Fig. 6 Diagrams For Evaluation Of Hybridization Of The PCR Products.

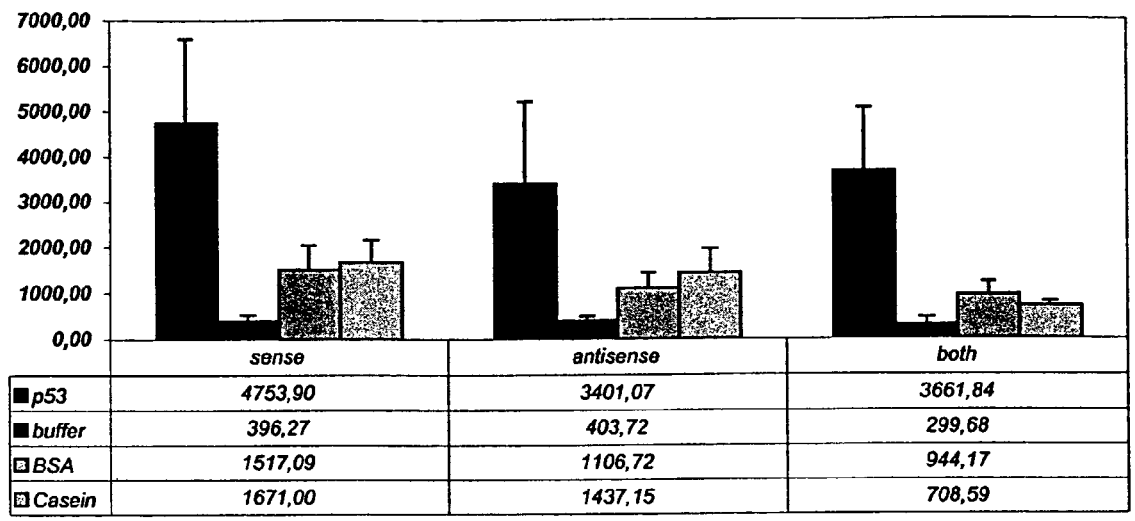
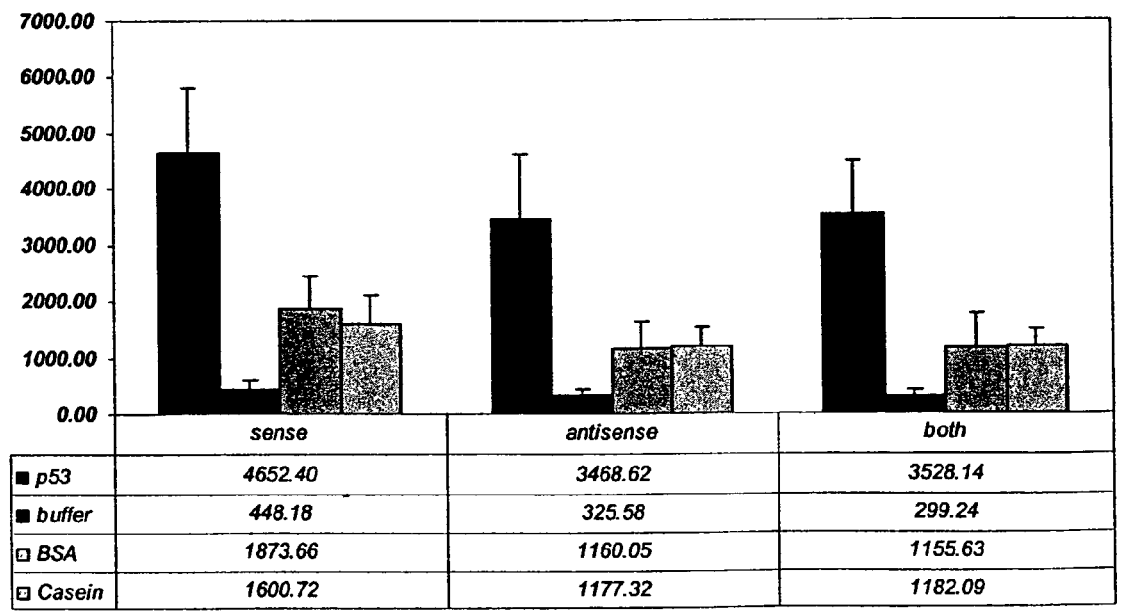
Fig. 7 Diagrams For Evaluation Of Hybridization Of The PCR Products.

```
                  SEQUENCE LISTING

<160> NUMBER OF SEQ ID NOS: 25

<210> SEQ ID NO 1
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 1
agaaacgctg gtgaaagt                                          18

<210> SEQ ID NO 2
<211> LENGTH: 19
<212> TYPE: DNA
<213> ORGANISM: unknown
<220> FEATURE:
<223> OTHER INFORMATION: TEM-1 Type b-lactamase gene

<400> SEQUENCE: 2
ctgaagatca gttgggtgc                                         19

<210> SEQ ID NO 3
<211> LENGTH: 20
<212> TYPE: DNA
<213> ORGANISM: unknown
<220> FEATURE:
<223> OTHER INFORMATION: TEM-1 Type b-lactamase gene

<400> SEQUENCE: 3
gacttggttg agtactcacc                                        20

<210> SEQ ID NO 4
```

-continued

```
<211> LENGTH: 17
<212> TYPE: DNA
<213> ORGANISM: unknown
<220> FEATURE:
<223> OTHER INFORMATION: TEM-1 Type b-lactamase gene

<400> SEQUENCE: 4
gccttgatcg ttgggaa                                                  17

<210> SEQ ID NO 5
<211> LENGTH: 17
<212> TYPE: DNA
<213> ORGANISM: unknown
<220> FEATURE:
<223> OTHER INFORMATION: TEM-1 Type b-lactamase gene

<400> SEQUENCE: 5
caccacgatg cctgtag                                                  17

<210> SEQ ID NO 6
<211> LENGTH: 17
<212> TYPE: DNA
<213> ORGANISM: unknown
<220> FEATURE:
<223> OTHER INFORMATION: TEM-1 Type b-lactamase gene

<400> SEQUENCE: 6
ctggagccgg tgagcgt                                                  17

<210> SEQ ID NO 7
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 7
gagccggtga gcgtgggt                                                 18

<210> SEQ ID NO 8
<211> LENGTH: 16
<212> TYPE: DNA
<213> ORGANISM: unknown
<220> FEATURE:
<223> OTHER INFORMATION: TEM-1 Type b-lactamase gene

<400> SEQUENCE: 8
tgggtctcgc ggtatc                                                   16

<210> SEQ ID NO 9
<211> LENGTH: 21
<212> TYPE: DNA
<213> ORGANISM: unknown
<220> FEATURE:
<223> OTHER INFORMATION: TEM-1 Type b-lactamase gene

<400> SEQUENCE: 9
tggatgaacg aaatagacag a                                             21

<210> SEQ ID NO 10
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 10
```

| | |
|---|---|
| agaaacgcta gtgaaagt | 18 |

<210> SEQ ID NO 11
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 11

| | |
|---|---|
| agaaacgctg gtgaaagt | 18 |

<210> SEQ ID NO 12
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 12

| | |
|---|---|
| agaaacgctc gtgaaagt | 18 |

<210> SEQ ID NO 13
<211> LENGTH: 18
<212> TYPE: DNA
<213> ORGANISM: unknown
<220> FEATURE:
<223> OTHER INFORMATION: TEM-1 Type b-lactamase gene

<400> SEQUENCE: 13

| | |
|---|---|
| agaaacgctt gtgaaagt | 18 |

<210> SEQ ID NO 14
<211> LENGTH: 20
<212> TYPE: DNA
<213> ORGANISM: Artificial Sequence
<220> FEATURE:
<223> OTHER INFORMATION: Primer for PCR probe

<400> SEQUENCE: 14

| | |
|---|---|
| atgagtattc aacatttccg | 20 |

<210> SEQ ID NO 15
<211> LENGTH: 20
<212> TYPE: DNA
<213> ORGANISM: Artificial Sequence
<220> FEATURE:
<223> OTHER INFORMATION: Primer for PCR probe

<400> SEQUENCE: 15

| | |
|---|---|
| ttaatcagtg aggcacctat | 20 |

<210> SEQ ID NO 16
<211> LENGTH: 20
<212> TYPE: DNA
<213> ORGANISM: Artificial Sequence
<220> FEATURE:
<223> OTHER INFORMATION: Primer for PCR probe

<400> SEQUENCE: 16

| | |
|---|---|
| atgagtattc aacatttccg | 20 |

<210> SEQ ID NO 17
<211> LENGTH: 20
<212> TYPE: DNA
<213> ORGANISM: Artificial Sequence
<220> FEATURE:

```
<223> OTHER INFORMATION: Primer for PCR probe

<400> SEQUENCE: 17
ttaatcagtg aggcacctat                                              20

<210> SEQ ID NO 18
<211> LENGTH: 15
<212> TYPE: DNA
<213> ORGANISM: Artificial Sequence
<220> FEATURE:
<223> OTHER INFORMATION: Primer for PCR probe

<400> SEQUENCE: 18
atggaggagc cgcag                                                   15

<210> SEQ ID NO 19
<211> LENGTH: 17
<212> TYPE: DNA
<213> ORGANISM: Artificial Sequence
<220> FEATURE:
<223> OTHER INFORMATION: Primer for PCR probe

<400> SEQUENCE: 19
tcagtctgag tcaggcc                                                 17

<210> SEQ ID NO 20
<211> LENGTH: 15
<212> TYPE: DNA
<213> ORGANISM: Artificial Sequence
<220> FEATURE:
<223> OTHER INFORMATION: Primer for PCR probe

<400> SEQUENCE: 20
atggaggagc cgcag                                                   15

<210> SEQ ID NO 21
<211> LENGTH: 17
<212> TYPE: DNA
<213> ORGANISM: Artificial Sequence
<220> FEATURE:
<223> OTHER INFORMATION: Primer for PCR probe

<400> SEQUENCE: 21
tcagtctgag tcaggcc                                                 17

<210> SEQ ID NO 22
<211> LENGTH: 28
<212> TYPE: DNA
<213> ORGANISM: Artificial Sequence
<220> FEATURE:
<223> OTHER INFORMATION: Primer for PCR probe

<400> SEQUENCE: 22
ggatatccac gtggaaggta gagaagac                                     28

<210> SEQ ID NO 23
<211> LENGTH: 26
<212> TYPE: DNA
<213> ORGANISM: Artificial Sequence
<220> FEATURE:
<223> OTHER INFORMATION: Primer for PCR probe

<400> SEQUENCE: 23
gaattctcac taagtagcag aaagca                                       26

<210> SEQ ID NO 24
```

-continued

```
<211> LENGTH: 28
<212> TYPE: DNA
<213> ORGANISM: Artificial Sequence
<220> FEATURE:
<223> OTHER INFORMATION: Primer for PCR probe

<400> SEQUENCE: 24
ggatatccac gtggaaggta gagaagac                                          28

<210> SEQ ID NO 25
<211> LENGTH: 26
<212> TYPE: DNA
<213> ORGANISM: Artificial Sequence
<220> FEATURE:
<223> OTHER INFORMATION: Primer for PCR probe

<400> SEQUENCE: 25
gaattctcac taagtagcag aaagca                                            26
```

METHOD FOR DETERMINING NUCLEOTIDE SEQUENCES

BACKGROUND OF THE INVENTION

The present invention relates to an improved method for determining nucleotide sequences on biochips/micro-assays, for example, using p53 mediated hybridization. The present invention relates particularly to the use of p53 polypeptides in determining changes in nucleotide sequences.

On the basis of data provided by the Human Genome Project (HUGO) and the findings regarding the genomic sequences of other organisms such as bacteria, increasing use of biochips or micro-arrays have been utilized for demonstration or investigation of such nucleotide sequences and, at the same time, a large number of different nucleotide sequences have been minutely tested.

Nucleotides of defined lengths or different sequences have been applied at pre-defined sites of a carrier and the carrier is then brought in contact with second nucleotide linked to an identifiable marker under conditions enabling binding of the second nucleotide preferentially to a nucleotide complementary thereto. After removal of non-hybridized nucleotides, detection of the marker at a defined position of the biochip or micro-array is an indication of the presence or absence of a property to be investigated.

As regards the current sequence data, it was found that certain characteristics of higher organisms, such as the tendency towards development of certain diseases or, in the case of the bacteria, the development of resistance to antibiotics, are based on a change only in a small number and in some cases only a single nucleotide ("single nucleotide polymorphism," SNP) in the sequence of the respective gene responsible therefore or involved therein. Therefore, there is an increased need for determining or demonstrating such changes in the genome of organisms in order to conduct, for example, population studies or forensic medical examinations or in order to demonstrate the presence of antibiotic-resistant bacteria.

At the present time, such minute changes in nucleotide sequences can be detected by means of various methods such as, for example, sequencing the nucleotide sequences of interest, restriction fragment length polymorphism (RFLP) analyses or allele-specific hybridization using longer probe sequences. Such methods, however, because of the inherent methodological and time expenditures in their performance, are unsuitable for screening of larger numbers of samples.

Although the use of biochips or micro-arrays in association with simple hybridization techniques would be desirable, the problem of specificity has not been satisfactorily resolved to date. In practice, it has been found to be extremely difficult to avoid selection of the probe-nucleotide or hybridization conditions so that hybridization of the probe-nucleotide using probe DNA that does not have a complementary nucleotide at the concerned site, i.e. the site to be investigated.

In order to solve these known problems of the prior art, the so-called "single nucleotide primer extension" method has been proposed. In this method, a short nucleotide sequence (the primer) is hybridized on the DNA to be investigated, which is applied onto a biochip/micro-array and then extended by one nucleotide using a DNA polymerase. An extension will occur in this procedure only if there is compatibility between the deoyxynucleotide triphospate presented with the complementary strand. The eventually elongated primers can be separated on the basis of their length on a gel or using their size with by means of MALDI (matrix-assisted laser desorption/ionization mass spectrometry).

According to an alternative embodiment, the deoxynucleotide triphosphate presented can be provided with a marker, so that the presence of the marker can be correlated directly with the presence of a particular nucleotide in the complementary strand.

Although this method eliminates several of the known problems, it is still costly, because it is a two-step procedure, and ultimately is limited to the determination of the presence of a single nucleotide change in a DNA sequence.

Thus, there continues to be a need for a method, by which a small number or even only a single nucleotide change in a nucleotide sequence can be determined.

SUMMARY OF THE INVENTION

An object of the present invention is, therefore, to overcome the drawbacks of the current technology and to provide a method, by which a large number of different samples can be investigated inexpensively and using which numerically small changes such as SNPs (single nucleotide polymorphisms) or two or three changes in a nucleotide sequence can be determined.

This object is achieved by a method for determination of nucleotide sequences, in which at least a first nucleotide is applied to a predetermined site on a carrier and the carrier is brought into contact with at least one second nucleotide under such conditions that enable hybridization of complementary strands, wherein the method is characterized in that the hybridization is carried out in the presence of a p53 polypeptide.

During the studies, which led to the present invention, it was unexpectedly found that p53 accelerates or promotes in vitro DNA-DNA hybridization even in the case of DNA that is immobilized on a carrier surface. On the basis of this finding, a novel and rapid DNA micro-array determination system was developed, by which even SNPs or a small number of changes in a nucleotide sequence of interest can be determined.

p53 itself is well known as a tumor suppressor protein. Its main function is known to be control of the cell division process, wherein the p53 protein binds to DNA as a transcription factor and thereby inaugurates the synthesis of other protein molecules that inhibit the cell cycle or contribute to driving the cell into apoptosis. The annealing activity also present in the p53 protein apparently also makes possible an improvement in hybridization of complementary nucleotide sequences in vitro.

Additional features and advantages of the present invention are described in, and will be apparent from, the detailed description of the presently preferred embodiments and the drawings.

BRIEF DESCRIPTION OF THE DRAWINGS

In the figures:

FIG. 2 represents a comparison of the fluorescence intensity obtain using current technology and using the method according to the invention.

FIG. 4 represents a print plan for the micro-array with amino-modified PCR-products; each step having been done using a volume of 200 ml/10 arrays. After immobilization, the blocked arrays could be stored in a dark, dry and cool atmosphere for three weeks. The block step was done in large. Petri dishes in the hybridization oven. 4 micro-arrays were always blocked together in one dish. The denaturing and washing step was done immediately before hybridization.

FIG. 5 represents the configuration of all variants simply amino-modified/bilaterally amino-modified PCR products in 3 x SSC and 1.5 M betain. Sequence matches were marked using the TEM β-lactamase-gene. All probes were printed in duplicate in order to prevent background effects. A sense amino-modified and Cy5-marked PCR product was used as positive print-control.

FIG. 6 represents diagrams for evaluation of hybridization of the PCR products. The concentration of 10 ng/µl and 15 ng/µl were evaluated. The experiments were done at 37° C.; the hybridization times varied. The first bars represent experiments using p53 addition; the third and fourth bars represent the non-specific protein addition and the second bar represents the negative control; in other words, without any protein.

FIG. 7 represents diagrams for evaluation of hybridization of the PCR products. The concentrations 15 ng/µl were evaluated for three different amino-modifications. The experiments were done at 37° C. for 1 hour. The first bars represent experiments using p53 addition; the third and fourth bars represent the non-specific protein addition and the second bar represents the negative control; in other words, without any protein.

DETAILED DESCRIPTION OF THE INVENTION

Figure 1:
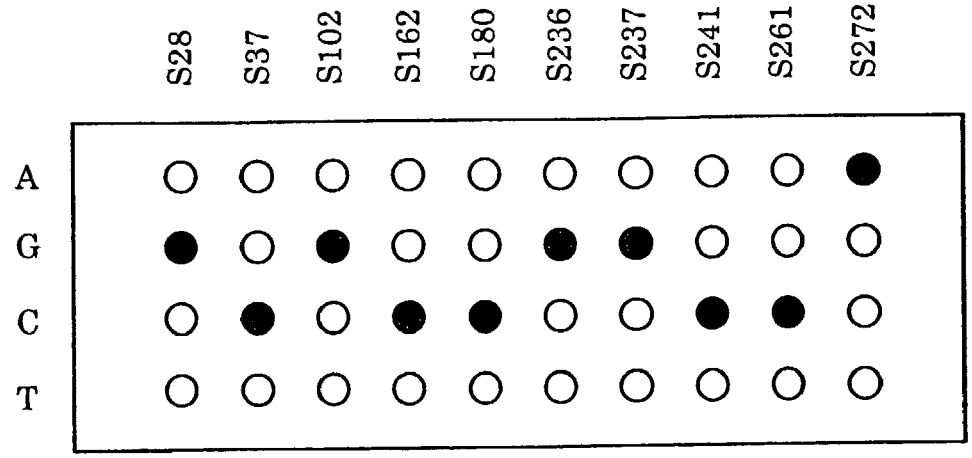
FIG. 1 represents a photographic representation of fluorescence obtained in the case of the micro-array.
Figure 1:
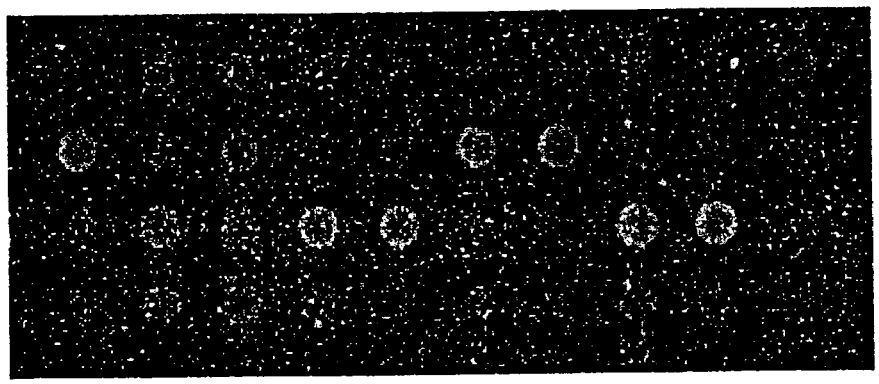

In the context of this application, the term "nucleotide" includes DNA and RNA, wherein they conventionally have adenine, cytosine, guanine, thymine and uracil as bases and deoxyribose and ribose as the structural sugar elements. Furthermore, a nucleotide can, however, also comprise any modified base known to current technology, which is capable of base pairing using at least one of the aforesaid bases. Further included in the term "nucleotide" are the derivatives of the aforesaid compounds, in particular derivatives having dyes of radioactive markers.

In the context of the invention, the nucleotides used as probes have a length from up to 2,000 nucleotides, preferably up to 100 nucleotides, more preferably 50 nucleotides and most preferably between 15 and 30 nucleotides. In the context of the present invention, target nucleotides are all nucleotides of any length; that is, up to the genomic sequence of an individual.

The carriers used according to the invention can be any commercially available carrier conventionally used for the purpose of hybridization, including membranes, metal carriers, plastic materials, beads or glass. A carrier with a larger number of applied nucleotides will be generally referred to as a biochip/micro-array.

Any process known from the prior art can be used for applying nucleotides to the carrier, which effects temporary or permanent immobilization, fixation or adhesion of the probe nucleotide to a site or in a region of the carrier; for example, by the formation of covalent, ionic, metallo-organic bonds, binding based on van der Waal's forces, or enzyme substrate interactions or so-called affinity binding. Naturally, any number of spacer molecules, for example polymer-based spacers, can be arranged between the carrier and the nucleotide applied on the carrier. Furthermore, carriers based on self-assembling layer systems are also suitable for the implementation of the present invention. Application can also be done by using automatic methods.

The p53 used in the invention can be any known p53 protein that promotes annealing of nucleotide strands. Along with native and recombinantly produced p53 from different organisms, any number of complexes or combinations thereof can be used, which comprise p53 or the region of p53 responsible for the annealing activity. In particular, p53-based holoenzymes come into consideration, which can be formed using other proteins. The present invention also includes thermally stable p53 variants, which can be produced using a random mutation process. This combination, which has increased thermal tolerance, is of advantage in the manufacture of thermally stable systems.

In comparison to the prior art, p53 hybridization can be done under somewhat different conditions relative to the salt concentrations, for example in a buffer containing less than 100 mmol/l of salt, NaCl or SSC or SSC, for example.

The method according to the invention can be used in any detection method known to date in the art, which is based on the method of hybridization of complementary nucleotide strands. According to the preferred embodiment, the method according to the invention can be used for determination of genetic mutations in organisms, since it is capable of quickly and highly specifically demonstrating several or even a single change in the sequence of a nucleotide. One of many examples of this is the determination of genetic mutations in different bacteria, for example, which occur in the TEM-1 β-lactamase gene. Furthermore, the method according to the invention is also suitable for the determination of genetic mutations, which occur in any number of organisms, including mammals and human beings. Similarly, for example, even synthetically manufactured nucleotide sequences can be investigated using the method according to the invention.

According to another preferred embodiment of the invention, the method according to the invention is used in the examination of a nucleotide for the presence of a single nucleotide polymorphism or SNP. SNP is defined as any polymorphism between two genomes, which is based on a single nucleotide substitution, a minor deletion or insertion. Specific SNPs correlated with an increased risk for the occurrence of a particular disease and are therefore of diagnostic interest.

According to another preferred embodiment, the method according to the invention is used for the determination of antibiotic resistance, since the resistance to antibiotica of certain bacteria is produced by genetic changes in the genome of the bacteria, in the wild type TEM-1 β-lactamase gene, for example. Approximately 70 mutations of this gene have already been described in the literature and a total of 28 potential mutation points were found in the wild type TWM-1 β-lactamase nucleotide sequence. Frequently, even a single or a small number of nucleic acid mutations due to SNPs have resulted in changed substrate specificity and inhibitor specificity of the β-lactamase, which can further result in accelerated breakdown of numerous antibiotics and consequently to the occurrence of antibiotic-resistance.

The method according to the invention thus makes it possible to ascertain resistance, for instance, of bacteria to the β-lactam antibiotics, penicillin, cephalosporines, and particularly to ampicillin.

In order to provide evidence of hybridization between a nucleotide applied to a carrier and a second nucleotide having a complementary sequence, at least one of these molecules has one or a plurality of detectable markers, for example dyes, particularly fluorescent dyes, or radioactive markers.

Obviously, p53 can better bind single-stranded DNA than to double-stranded DNA in vitro, such that p53 after formation of a double-strand moves towards single-stranded DNA. This property represents a significant advantage in the case of hybridizations, in which, for example, due to equipment-related or reaction reasons mixing is done by diffusion or gentle stirring or pumping of the solutions. Use of p53 is also advantageous, if only small quantities of a nucleotide of interest are present.

The present invention further includes a kit for performing a procedure disclosed in the claims, which contains a p53 polypeptide. The most widely varying embodiments of such a kit can be realized such that, for example, micro-arrays/biochips can be used in medical laboratories, which make possible routine determination of genetic mutations, whether in the identification of diseases or for determining antibiotic resistance, or prepared reaction containers, which contain p53 and a dye-labeled nucleotide, whereby serially performed, spectroscopic measurements can be facilitated.

In particular, the method according to the invention is can be used for rapid tests for determination of genes coding for antibiotic resistance. This makes it possible for patients to be provided quickly, in 30-60 minutes, with an antibiotic with a high probability of effectiveness.

Such rapid tests are used, for example, to determining, whether mutations of TEM-1 β-lactamase are present on the gene. As a result of these mutations, several TEM derivatives have activity against more recent antibiotics and are designated as "extended-spectrum beta-lactamase" (ESBL). ESBL enzymes have been observed, for example, in *Klebsiella pneumoniae*, but also in *Enterobacteriaceae, Citrobacter* and *Salmonella* species. As a result, the use of various, well-known antibiotics is appropriate only after prior testing for resistance.

The test methods according to the invention thus make it possible that cost-effective standard antibiotics can be used more frequently and newly developed, highly effective antibiotics have to be used less frequently and consequently are available to the public longer for patients with multiply resistant bacterial infections.

The following examples explain the invention, while not limiting it. In particular, the sequence lengths described therein of the first and second nucleotide and the dye labeling of the second nucleotide do not limit the present invention.

Example 1

Examination of SNPs in the TEM-1 β-lactamase Gene

General Structure of the Micro-array Configuration

Four sets of probes are prepared corresponding to the four nucleotides A, G, C and T occurring in DNA and each arranged at a particular position of the micro-array for the know mutant positions S28, S37, S102, S162, S180, S236, S237, S241, S261 and S272 in the DNA of the TEM-1 β-lactamase gene (see below).

The sequences are given in the following Table I:

TABLE I

| Nucleotide Sequence | Name: | SEQ ID NO: |
|---|---|---|
| agaaacgctGgtgaaagt | S28 | 1 |
| ctgaagatCagttgggtgc | S37 | 2 |
| gacttggttGagtactcacc | S102 | 3 |
| gccttgatCgttgggaa | S162 | 4 |
| caccacgaTgcctgtag | S180 | 5 |
| ctggagccGgtgagcgt | S236 | 6 |
| gagccggtGagcgtgggt | S237 | 7 |
| tgggtctCgcggtatc | S241 | 8 |
| tggatgaacgaAatagacaga | S272 | 9 |

The nucleotide sequence of the probe was derived from the TEM 1 type β-lactamase gene (GENEBANK®, AF309824). The underlined nucleotides exhibit point mutations.

With reference to FIG. 1, thereof, to probe set for the S28 mutation is in the first column and has the following four sequences:

aga aac gct agt gaa agt    (S28_a)    (SEQ ID NO. 10)

aga aac gct ggt gaa agt    (S28_pg)   (SEQ ID NO. 11)

aga aac gct cgt gaa agt    (S28_c)    (SEQ ID NO. 12)

aga aac gct tgt gaa agt    (S28_t)    (SEQ ID NO. 13)

One of these probes of the S28 probe set (S28_pg) corresponds to the respective section of wild type TEM-1 β-lactamase DNA, while the others represent point mutations at the concerned site.

Production of the Carrier Assemblies

The respective nucleotides were collected in a solution (45 mM sodium citrate, 450 mM NaCl, 1.5 M betain). Thus a concentration of 20 pmol/μl of nucleotide/DNA probe was obtained. The solution (30 μl) was applied in the form of spots onto poly-L-lysine coated glass slides (poly PREP slides, Sigma).

After drying overnight at room temperature, the slides were heated for 5 seconds on a metal block to 80° C. Binding (cross-linking) of the DNA to the slide surface was achieved by UV irradiation at a total energy of 100 mJ using a BLX 254 UV crosslinker system (Biometra). The slide obtained in this way was then installed for one hour in a blocking solution (1 g succinic acid, 200 ml 1,2-dichloroethane (DCE), 2.5 ml 1-methylimidazole) and then washed in DCE. After a short rinsing operation with 95% ethanol, the slides were dried at room temperature. For a second blocking process, 12 μl of ultrasound-treated salmon sperm DNA (0.01 μg/μl, Stratagene) were applied the slides, which were then incubated for 30 minutes under a glass cover at room temperature in a humid chamber. After removal of the glass cover, the slides were dried with the aid of nitrogen gas.

Production of the Target DNA

The target DNA (part of the β-lactamase gene) was produced using a PCR (polymerase chain reaction) with fluorescent dye labeled nucleotide.

The reaction mixture contained 10 μl PCR buffer (10×PCR buffer, Fermentas), 10 μl 25 mM, MgCl$_2$ solution (Fermentas), 2 μl forward and reverse primer (20 μmol/μl) (atgagtat-tcaacatttccg (SEQ ID NO: 16): Forward primer; ttaatcagtgag-gcacctat (SEQ ID NO: 17): Reverse primer), 1 μl 25 mM, dNTPs (2'-deoxyribonucleoside-5'-triphosphate), 0.5 μl 25 nM CY™5-dCTP ( . . . -deoxycytidine-5'-triphosphate (FLUOROLINK™ Cy5-dCTP, 5-amino-propargyl-2'-deoxycytidine 5'-triphosphate coupled to Cy5 fluorescence dye (Cy5-AP3-dCTP), Amersham Pharmacia), 1 μl Taq DNA polymerase (1 U/μl, Eppendorf) and 1 μl of the template DNA (0.1 μg/μl) (plasmid pUC 19, Merck).

The PCR reaction was done in a MASTERCYCLER® system (Eppendorf) using the following program: 95° C., 1 min; 25 cycles at 95° C. 30 sec, 55° C. 30 sec, 72° C. 60 sec and 72° C. 4 min.

After cleaning by ethanol precipitation (0.3 M sodium acetate, 2× volume 95% ethanol; 20 min at −21° C.), centrifugation at 20,000 g, and dissolution of the pellets in water over 5 minutes at room temperature the PCR product was incubated (45 μl PCR product, 5 μl buffer (RQ1 reaction buffer, Promega), 1 μl RQ1 DNase solution (1 U/μl, Promega). The reaction was arrested by the addition of 5 μl of a stop solution (RQ1 stop buffer, Promega) and then incubated for 10 min at 65° C.

Hybridization a) Prior Art

The target DNA was diluted, and mixed with the hybridization solution (×6 SSPE (saline sodium phosphate EDTA); (×20, 3.6 M NaCl, 0.2 M sodium phosphate, 20 mM EDTA (ethylene diamine tetraacetate), 0.1% formamide as final concentration (v/v %) until reaching a final volume of 12 ml.

Hybridization was done at 45° C. over 6-12 hours. Then the slides were washed once using a 0.1% (w/v %) using a X2 SSC (saline sodium citrate) buffer solution containing SDS (sodium dodecyl sulfate) for 5 minutes, then once in a X0.2 SSC buffer solution for 3 minutes at room temperature and then dried under nitrogen.

b) p53 Mediated Hybridization 0.5 μl p53 (1 μg/μl, Santa Cruz) was diluted with 11.5 μl annealing buffer (5 mM MgCl$_2$, 10 mM KCl, 5 mM phosphate buffer, 0.5 mM EDTA, 3.5% (v/v %) glycerin) and then added to a glass-covered micro-array. After incubation at room temperature for 10 minutes, the glass cover was removed and 1 μl target DNA (target DNA incubated with DNAse I; see above), which had been mixed with 12 μl of annealing buffer (above), were applied to the micro-array. After hybridization for 30 minutes at 37° C., the slide was washed with X2 SSC (0.03 M sodium citrate, 0.3 M sodium chloride pH 7.0), 0.1% SDS for 10 minutes and rinsed with X0.2 SSC for 3 minutes at room temperature. The glass slides were then dried with nitrogen and examined using a laser scanner for fluorescence.

c) Quantification of Positive Spots

The micro-array was scanned using a laser scanner (GMS 418, Genetic Microsystems) for determination of the presence of hybridization on the respective spots of the micro-array. A calculation of the intensity of the fluorescence emitted by a spot was done using an imaging software (IMAGENE® Ver. 3, BioDiscovery, Inc.). Each experiment was repeated six times.

Figure 3:
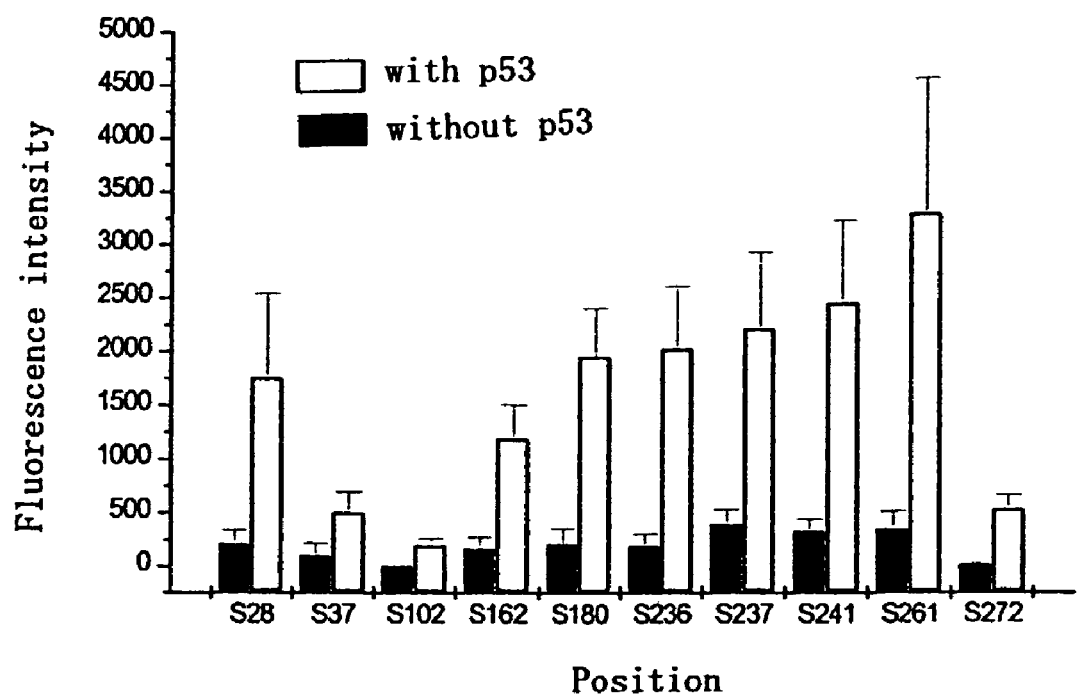
FIG. 3 represents a table with the fluorescent intensities converted to percentages.

FIG. 3 graphically represents the results obtained, wherein the white bars show the results obtained using the method according to the invention and the black bars the intensities obtained using the prior art method.

Example 2

PCR Product Micro-Array

Preparation of the Micro-Array a) Development of PCR Product Probes

In the case of the PCR product probes for detecting antibiotic resistance in general, the entire TEM1-β-lactamase gene (861 bp) is concerned and is used for detecting resistance against ampicillin (AMP). The tetracycline resistance gene (tet) (1,500 bp) is used as the negative control. The gene from p53 (approx. 1,000 bp) and the huAchE gene (1,400 bp) was used in checking for non-specific hybridizations.

| | Plasmids Used | |
|---|---|---|
| Source | Plasmid/Insert Construct | Gene |
| E.coli | Puc19 | TEm1 - β-lactamase ampicillin resistance gene |
| E.coli | pACYC184 | Tetracycline resistance gene |
| E.coli DH5α | pORF-hp53 | p53 |
| | | huAChE | b) DNA Isolation-using the QIAPREP® Spin Miniprep Kit

Using the QIAAMP® from Qiagen, the DNA was isolated from a ON culture (2 ml sterile LB medium diluted with 2 μl 100 mm ampicillin and 100 μl glycerol stock ON incubated at 37° C.). The procedure was done according to the manufacturer's instructions; the required buffers were included in the supply.

The cell pellet harvested by centrifuging (20,000 g for 30 s) was carefully resuspended in 250 μl of P1 buffer and mixed with P2 buffer by carefully shaking three times. 350 μl N3 buffer was then added. Then the mixture was centrifuged (10 min at 20,000 g and 4° C.). The extracted DNA in the supernatant was then applied to QIAAMP® mini-column that had been previously installed in a collection tube and centrifuged for 30 s at 20,000 g. After the subsequent washing operation using 750 μl PE buffer and followed by centrifuging (20,000 g for 1 min) the DNA was eluted using TE buffer or HPLC H$_2$O into 1.5 ml microcontainer. These minipreps were used as the template for the amplification.

c) Determination of DNA Concentration

After 1:50 dilution using 1×TE, the DNA concentration of a DNA miniprep was determined photometrically in an Eppendorf BioPhotomoeter against a control value of 1×TE at 260 nm.

d) Probe Preparation Using the Polymerase Chain Reaction

The DNA used in this study for producing the probes for PCR product micro-arrays are listed in Table II.

They were produced by amplification using the planned primers (Table).

TABLE II

| Name: | Purpose | Sequence | Modification | SEQ ID NO: |
|---|---|---|---|---|
| Amp | Forward primer | 5'-ATGAGTATTCAACATTTTCCG-3' | 5' Amino | 14 |
| Amp | Backward primer | 5'-TTAATCAGTGAGGCACCTAT-3' | 5' Amino | 15 |
| Amp | Forward primer | 5'-ATGAGTATTCAACATTTCCG-3' | | 16 |
| Amp | Backward primer | 5'-TTAATCAGTGAGGCACCTAT-3' | | 17 |
| Tet | Forward primer | | 5' Amino | |
| Tet | Backward primer | | 5' Amino | |
| Tet | Forward primer | | | |
| Tet | Backward primer | | | |
| p53 | Forward primer | 5'-ATGGAGGAGCCGCAG-3' | 5' Amino | 18 |
| p53 | Backward primer | 5'-TCAGTCTGAGTCAGGCC-3' | 5' Amino | 19 |

TABLE II-continued

| Name: | Purpose | Sequence | Modification | SEQ ID NO: |
|---|---|---|---|---|
| p53 | Forward primer | 5'-ATGGAGGAGGCGCAG-3' | 5' Amino | 20 |
| p53 | Backward primer | 5'-TCAGTCTGAGTCAGGCC-3' | | 21 |
| HUAChE | Forward primer | 5'-GGATATCCACGTGGAAGGTAGAGAAGAC-3' | 5' Amino | 22 |
| HuAchE | Backward primer | 5'-GAATTCTCACTAAGTAGCAGAAAGCA-3' | 5' Amino | 23 |
| HuAchE | Forward primer | 5'-GGATATCCACGTGGAAGGTAGAGAAGAC-3' | | 24 |
| HUAChE | Backward primer | 5'-GAATTCTCACTAAGTAGCAGAAAGCA-3' | 5' Amino | 25 | e) Amplification

The complete PCR products were amplified using the respective primer pair from the DNA extracts by means of PCR in the Eppendorf MASTERCYCLER®. Both the normal primers and the 5 amino-modified primers were used for producing the probes. A 100 µL preparation contained the following components:

TABLE III

PCR Preparation of an Amplification for Production of Probes

| | |
|---|---|
| Template (approx. 10 ng/µl) | 1 µl |
| dNTPs (2.5 mM) | 10 µl |
| 25 mM MgCl$_2$ | 10 µl |
| 10x PCR buffer | 10 µl |
| Forward Primer 1 (20 µM) | 2 µl |
| Reverse Primer 2 (20 µM) | ..2 µl |
| Tag polymerase (100 U) | 1 µl |
| HPLC-H$_2$O | ad 100 µl |

PCR was done according to the following program:

TABLE IV

PCR Program for Amplification of Any DNA used in this Study

| Cycles | Denaturing | Annealing | Elongation |
|---|---|---|---|
| 1 | 94° C./60 s | | |
| 25 | 95° C./30 s | 55° C. 30 s | 72° C. 1 min |
| 1 | | | 72° C. 4 min | f) Target Preparation Using a Polymerase Chain Reaction

In the case of the target DNA used in this study for hybridization of the micro-arrays, it was exclusively the commercially obtainable TEM1-β-lactamase gene contained in puc19.

g) Amplification and Fluorescence Labeling

The complete TEM1 β-lactamase gene with a length of 652 bp with the respective primer pair (Table) from DNA extracts was amplified using a PCR in the ROBOCYCLER™ (Stratagene) and fluorescent labeled using Cy5-dCTP. A 100 µL preparation contained the following components:

TABLE V

| | |
|---|---|
| Template (in puc19) | 1 µL |
| dNTPs (2.5 mM for dATP, dGTP, dTTP 1.7 mM for dCTP) | 2 µL |
| 25 mM MgCl$_2$ | 10 µL |
| 10x PCR buffer | 10 µL |
| Cy5-dCTP (25 nM) | 2 µL |
| Forward Primer 1 (20 µM) | 2 µL |
| Reverse Primer 2 (20 µM) | ..2 µl |
| Tag polymerase (100 U) | 1 µl |
| HPLC-H$_2$O | ad 100 µl |

The same program was used here as in the case of the normal amplification (above).

h) Clean up of DNA

The clean up of fluorescent-labeled PCR product and unmarked PCR product was done using QIAQUICK® mini-columns (Qiagen). The procedure was done according to the manufacturer's instructions; the buffers were included in the supply. The centrifuging parameters were 1 minute and 20,000 g in each step. A 100 ml PCR preparation was added with 500 µl PB buffer on a QIAAMP® mini-column, which was installed in a collection tube and centrifuged. After a washing step using 75 µl PE buffer and again centrifuging, all liquid was removed from the collection tube and a final centrifuging step was done to complete removal of the washing buffer. The DNA was then eluted using centrifugation in 32 µl TE buffer into 1.5 ml micro-container. Control was done using 1% agarose gels.

i) Hybridization in Amino-modified PCR Products

Experiment Using p53

140 ng cleaned up, fluorescent-labeled target DNA were mixed with an appropriate quantity of 20×SSPE and diluted to a hybridization volume of 13.5 µl with HPLC-H$_2$O. The final concentration of SSPE was thus 1×SSPE or 165 mM in the experiment. Immediately after three minute denaturing at 95° C. and immediate cooling on ice, this solution was diluted with 0.5 µl p53 (Santa Cruz) (c=1 µg/µl) and pipetted onto the micro-arrays and covered with a cover glass (18×18 mm), while avoiding bubbles. The arrays were then sealed in moisture-tight hybridization chambers (Corning), which were filled with 10 µl HPLC-H$_2$O each in the two supply containers. Hybridization followed immediately at 37° C. in a hybridization oven. The hybridization times were 1 hour, 30 minutes and 10 minutes.

Experiment Using BSA and Casein

For control for non-specific protein effects, the experiment was performed as described above. Instead of p53, exactly the same concentration of BSA or casein was added. Both proteins were dissolved in the same storage buffer as the protein p53 supplied by Santa Cruz.

Experiment Using Storage Buffer

As a negative control of the experiment, only the manufactured storage buffer of the p53 protein was used. The following buffers and solutions were used.

| 20x SSPE | |
|---|---|
| NaCl | 175.5 g |
| Na$_2$HPO$_4$.H$_2$O | 27.6 g |
| Na$_2$EDTA | 7.4 g |
| ddH$_2$O | ad 1000 ml |
| | pH 7.4 |

-continued

| Rinsing Buffer I | | |
|---|---|---|
| 100% Triton X100 | 2 ml | 0.1% Triton X100 |
| ddH$_2$O | ad 2000 ml | |
| Heating to 60° C. | | |
| Rinsing Buffer II | | |
| 32% HCl | 1 ml | 0.016% |
| ddH$_2$O | ad 2000 ml | |
| Rinsing Buffer III | | |
| 1 M KCl | 200 ml | 100 mM KCl |
| ddH$_2$O | ad 2000 ml | |
| 20x SSC | | |
| NaCl | 175.3 | |
| Na$_3$Citrat.2H$_2$O | 88.2 g | |
| ddH$_2$O | ad 1 000 ml | |
| Na$_2$EDTA | pH 7.0 | |
| p53 Storage Buffer | | |
| 87% Glycerol | 57.5 μl | 50% |
| 50 mM DTT | 10 μl | 5 mM |
| 10xPBS | 10 μl | 1x |
| ddH$_2$O | ad 100 μl | |
| p53 Storage Buffer with Protein | | |
| 87% Glycerol | 57.5 μl | 50% |
| 50 mM DTT | 10 μl | 5 mM |
| 10xPBS | 10 μl | 1x |
| 10 μg/μL BSA/Casein | 10 μl | 1 μg/μL |
| ddH$_2$O | ad 100 μl | | k) Washing and Drying Amino-modified PCR Product Arrays

Following hybridization, 10 arrays washed in washing buffer I (2×SSC+0.1% SDS in ddH$_2$O) and then for a further 10 minutes in washing buffer Ia (2×SSC) and then for a further 10 minutes in washing buffer II (0.2×SSC in ddH$_2$O) (see under 0) by shaking. The arrays were immediately dried in an N$_2$ current and then placed in the GMS 418 array scanner for detecting.

l) Results

For each experiment three micro-arrays were used. In other words, each bar represents generally a total of 18 values, since duplicates were printed on one subarray and three subarrays were on each slide. Here, too, only the sense amino-modification was evaluated, since essentially the same values were obtained for anti-sense and sense.

The signal intensities for 10 and 15 ng/μl were evaluated in FIG. 6. It can be seen, that the values for the p53 experiments were clearly higher than for the negative controls or in the case of using BSA and casein. The normally required hybridization time for PCR products is generally 6-10 hours. According to the invention signals that could be evaluated were obtained already after 10 minutes of hybridization time.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for determining the presence of at least one single nucleotide polymorphism at a nucleotide position in a first nucleotide sequence comprising
providing a microarray having a plurality of second nucleotide sequences fixed at a predetermined site on said microarray, wherein each of said second nucleotide sequences is complementary to the first nucleotide sequence except for a single substitution of a different nucleotide at a position corresponding to the nucleotide position of the single nucleotide polymorphism in the first nucleotide sequence and wherein each of said second nucleotide sequences is between 15-30 nucleotides in length;
hybridization of nucleotides of the first nucleotide sequence with said plurality of complementary second nucleotide sequences of the microarray, wherein said hybridization is performed in the presence of a p53 polypeptide and at a temperature of about 37° C.; and
determining the presence of hybridization between nucleotides of said first nucleotide sequence and said plurality of complementary second nucleotide sequences of the microarray to indicate the presence of said at least one single nucleotide polymorphism.

2. The method according to claim 1, wherein the first nucleotide sequence is a DNA.

3. The method according to claim 1 including determining a resistance to an antibiotic, wherein the first nucleotide sequence is included in a resistance gene associated with conferring resistance to the antibiotic.

4. The method according to claim 3, wherein the resistance to an antibiotic is chosen from the group consisting of β-lactam antibiotic resistance, penicillin antibiotic resistance, cephalosporin antibiotic resistance, and ampicillin resistance.

5. The method according to claim 1, wherein the first nucleotide sequence is radioactive-labeled.

6. A method for determining the presence of a single nucleotide polymorphism in a first nucleotide sequence comprising
providing a microarray having a known nucleotide sequence fixed at a predetermined site on said microarray, wherein said known nucleotide sequence is complementary to the first nucleotide sequence except for a single substitution of a different nucleotide at a position corresponding to the nucleotide position of the single nucleotide polymorphism in the first nucleotide sequence, and wherein said known nucleotide sequence is between 15-30 nucleotides in length;
contacting the microarray with the first nucleotide sequence under conditions that enable hybridization of nucleotides of the first nucleotide sequence with said complementary known nucleotide sequence of the microarray, wherein said hybridization is performed in the presence of a p53 polypeptide and at a temperature of about 37° C.; and
determining the presence of hybridization between nucleotides of said first nucleotide sequence and said complementary known sequence of the microarray to indicate the presence of the single nucleotide polymorphism.

7. The method according to claim 1, wherein the first nucleotide sequence is an RNA.

8. A method for determining resistance to an antibiotic comprising
determining the presence of at least one single nucleotide polymorphism at a nucleotide position in a nucleotide sequence of a resistance gene, wherein said resistance gene is associated with conferring resistance to the antibiotic, and wherein determining the presence of said at least one single nucleotide polymorphism includes
providing a microarray having a plurality of second nucleotide sequences fixed at a predetermined site on said microarray, wherein each of said second nucleotide sequences is complementary to the resistance gene nucleotide sequence except for a single substitution of a different nucleotide at a position corresponding to the nucleotide position of the single nucleotide polymorphism in the resistance gene nucleotide sequence, wherein each of said second nucleotide sequences is between 15-30 nucleotides in length,
contacting the microarray with the resistance gene nucleotide sequence under conditions that enable hybridization of the nucleotides of the resistance gene nucleotide sequence with said plurality of complementary second nucleotide sequences, wherein said hybridization is performed in the presence of a p53 polypeptide and at a temperature of about 37° C., and
determining the presence of hybridization between nucleotides of said resistance gene nucleotide sequence and said plurality of complementary second nucleotide sequences to indicate the presence of said at least one single nucleotide polymorphism, said at least one single nucleotide polymorphism indicating resistance to the antibiotic.

9. The method according to claim 8, wherein the resistance to antibiotic is selected from the group consisting of β-lactam antibiotic resistance, penicillin antibiotic resistance, cephalosporin antibiotic resistance, and ampicillin resistance.

10. The method according to claim 1, wherein the first nucleotide sequence is fluorescence-labeled.

11. A method for determining at least one genetic mutation at a nucleotide position in a first nucleotide sequence of an organism comprising providing a microarray having a plurality of second nucleotide sequences fixed at a predetermined site on said microarray, wherein each of said second nucleotide sequences is complementary to the first nucleotide sequence except for a single substitution of a different nucleotide at a position corresponding to the nucleotide position of the genetic mutation in the first nucleotide sequence, wherein one of said second complementary nucleotide sequences is a wild-type sequence of the organism, and wherein each of said second nucleotide sequences is between 15-30 nucleotides in length;

contacting the microarray with the first nucleotide sequence under conditions that enable hybridization of nucleotides of the first nucleotide sequence with said plurality of complementary second nucleotide sequences of the microarray, wherein said hybridization is performed in the presence of a p53 polypeptide and at a temperature of about 37° C.; and determining the presence of hybridization between nucleotides of said first nucleotide sequence and said plurality of complementary second nucleotide sequences of the microarray to indicate the presence of the genetic mutation.

* * * * *